United States Patent [19]

Langdon

[11] Patent Number: 4,504,418
[45] Date of Patent: Mar. 12, 1985

[54] NON-IONIC SURFACE-ACTIVE AGENTS COUPLED WITH CARBONATES OR CARBOXYLIC ESTERS

[75] Inventor: William K. Langdon, Grosse Ile, Mich.

[73] Assignee: BASF Wyandotte Corporation, Wyandotte, Mich.

[21] Appl. No.: 223,877

[22] Filed: Jan. 9, 1981

[51] Int. Cl.$^3$ .................. C07C 69/96; C07C 69/34
[52] U.S. Cl. ................................ 260/463; 560/130; 560/146
[58] Field of Search ............... 560/1, 8, 149, 129, 560/130, 146; 260/463; 568/625

[56] References Cited

U.S. PATENT DOCUMENTS 3,676,398  7/1972  D'Alelio .................. 560/129

Primary Examiner—Henry R. Jiles
Assistant Examiner—Robert C. Whittenbaugh
Attorney, Agent, or Firm—Bernhard R. Swick

[57] ABSTRACT

Biodegradable non-ionic surface-active agents containing carbonate groups or residues of carboxylic esters can be prepared by reacting hydrophilic polyoxyalkylene glycols derived from the same or different alkylene oxide glycols with monofunctional alcohols. The compositions of the invention contain both hydrophilic and hydrophobic groups in the molecule making them suitable for use as surface-active agents. The residues of the monofunctional alcohols provide hydrophobic groups in the molecule of the surface-active agent.

9 Claims, No Drawings

NON-IONIC SURFACE-ACTIVE AGENTS COUPLED WITH CARBONATES OR CARBOXYLIC ESTERS

BACKGROUND OF THE INVENTION

1. Field of the Invention

This invention relates to non-ionic surface-active agents containing carbonate and carboxylic ester groups.

2. Description of the Prior Art

A wide variety of non-ionic surface-active agents are known in the art. Usually, these are stable in acid, basic and neutral media. In addition, many non-ionic surface-active agents are not easily biodegraded making such surface-active agents a source of water pollution. In some applications, it is necessary or at least highly desirable to modify or change the surface activity of a surface-active agent at some critical point in an operation utilizing such agents. For example, in the recovery of oil and waxes from raw wool by emulsification there is obtained an emulsion in water which is not easily broken so as to allow recovery of the oils and waxes for the purposes of disposal. In addition, commercial laundry effluents containing non-ionic surface-active agents are a source of water pollution. In the recovery of petroleum, emulsions are formed which are not easily broken without the use of certain complex and expensive demulsifying agents.

The present surface-active compounds are suited for use under the conditions described above and yet can be changed in surface activity properties by treatment with a dilute basic compound and/or heating in order to degrade the surface-active compounds by hydrolytic cleavage of the molecule. The present compounds can be made so as to exhibit low or high foaming, good detergency, and low or high cloud points as desired.

In U.S. Pat. No. 4,072,704, there are disclosed multi-block coupled polyoxyalkylene copolymer surfactants prepared by reacting bifunctional compounds to form polycarbonate esters. These materials are formed of polyoxyalkylene units coupled by reaction with an alkyl carbonate such as diethyl carbonate. There is no indication that monofunctional alcohols are useful in the preparation of such surfactants. Biodegradable, alkali-stable, non-ionic surfactants are disclosed in U.S. Pat. No. 4,207,421 as containing the residues of a linear aliphatic alcohol, ethylene oxide, and a propylene oxide or butylene oxide residue cap.

High molecular weight polycarbonates are disclosed in U.S. Pat. No. 3,248,414; U.S. Pat. No. 3,248,415; and U.S. Pat. No. 3,248,416. These are prepared, for instance, by reacting ethylene carbonate and ethylene oxide in the presence of a basic catalyst. The hydroxyl-terminated compositions range in molecular weight from 700 to 5000 and react with isocyanates to form urethanes.

SUMMARY OF THE INVENTION

It has now been discovered that non-ionic surface-active agents can be prepared having surface-active properties which can be destroyed or changed by exposure to heat and/or basic conditions. These are carbonate-coupled or carboxylic ester-coupled polyoxyalkylene glycols containing at the terminal portions of the molecule, at least one hydrophobic group derived from a monofunctional alcohol. The polyoxyalkylene glycols which are coupled can be hydrophilic or predominantly hydrophilic mixtures of hydrophobic and hydrophilic glycols derived from the polymerization of mixtures of ethylene oxide and a higher alkylene oxide. The polyoxyalkylene glycols can thus be homopolymers or derived from block copolymers or heteric copolymers prepared by reacting alkylene oxides having 2 to 4 carbon atoms with a base compound containing at least one active hydrogen. In order to provide surface-activity, the surfactant molecule must contain both hydrophilic and hydrophobic groups. The hydrophobic group is the residue of an aliphatic, aromatic or mixed aliphatic-aromatic group, i.e., a fatty alcohol and is present as at least one terminal hydrophobic group.

The surfactant compositions of the invention are unexpectedly formed by a selective coupling reaction in which a hydrophobic monofunctional alcohol, for instance, is coupled with a hydropilic polyoxyalkylene glycol, as indicated by the water-solubility of the product obtained, rather than the expected random coupling of each of the reactants such that insoluble species are formed. The surfactants of the invention can be easily prepared by admixing all the reactants in a reaction zone and heating the reactants to reflux temperature in the presence of an alkaline catalyst and a lower alkyl ($C_1$-$C_7$) carbonate ester or dicarboxylic acid alkyl ester having 2 to 6 carbon atoms in the acid portion and 1 to 7 carbon atoms in the alkyl ester portion. The alkyl alcohol produced in the reaction is removed by distillation and the crude reaction product is stripped free of unreacted materials to provide the product desired.

Because the carbonate- and dicarboxylic acid ester-linked surfactants of the invention are sensitive to hydrolytic cleavage under basic conditions and/or elevated temperatures, the surface-active characteristics can be destroyed or changed by exposure to conditions which promote hydrolytic cleavage of the molecule. Thus, the surfactants of the invention containing ester linkages are more desirable from an ecological standpoint than the many nonionic surface-active agents previously known in the art which are extremely resistant to biodegradation as well as degradation under both acid or basic conditions.

Detailed Description of the Invention

This invention relates to non-ionic surface-active compositions containing carbonate ester or dicarboxylic acid ester linkages in addition to the usual ether linkages present in most non-ionic surface-active agents. As a consequence of the presence of the ester linkages, the surface-active agents of the invention are more susceptible to hydrolytic cleavage as compared to most non-ionic surface-active agents known in the prior art.

In accordance with this invention, polyoxyalkylene polymers and monofunctional aliphatic, aromatic or aliphatic-aromatic alcohols can be coupled to prepare surface-active agents terminated on at least one end of the molecule with the hydrophobic group residue of the monofunctional alcohol. Preferably, the molar quantities used of the carbonate or dicarboxylic acid ester coupling agents equal those quantities of the polyoxyalkylenes utilized in order to provide a single terminal alcohol residue. Where each terminal portion of the molecule contains the residue of the alcohol, more coupling agent is required, namely, up to 1.5 moles thereof based upon the molar quantity of the polyoxyalkylenes utilized.

The surface-active compounds of the invention have the formulas

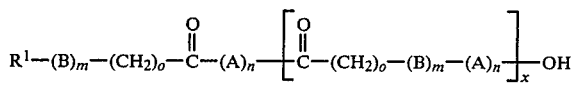
(I)

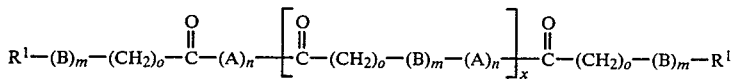
(II)

wherein $R_1$ is the residue of at least one hydrophobic monofunctional organic alcohol derived from a compound selected from the group consisting of at least one of an aliphatic alcohol, an arylalkyl alcohol, alkoxylated derivatives thereof, alkoxylated aryl alcohols, and alkoxylated alkylaryl alcohols, wherein A is the residue of at least one hydrophilic oxyalkylene polymer derived from the same or different alkylene oxides wherein said polymer is selected from at least one of the group consisting of homopolymer or copolymer (heteric or block) polyalkylene glycols derived respectively from the reaction of an alkylene oxide having 2 carbon atoms, ethylene oxide, or at least two alkylene oxides having 2 to 4 carbon atoms with an active hydrogen compound having at least two active hydrogen atoms, and wherein B is C=O, m is 0 or, X is an integer of 1 to 20, preferably an integer of 1 to 10, n is individually selected from integers such that the molecular weight is about 104 to about 1000, o is an integer of 0 to 4, and when o is 0, m is 0.

The coupling reaction utilizing a dialkyl carbonate or dicarboxylic acid ester can be carried out at a temperature in the range of about 100° to 200° C. in the presence of an alkaline catalyst. Examples of such catalysts are sodium carbonate, potassium carbonate, sodium methoxide, sodium ethoxide, potassium ethoxide, sodium hydroxide, potassium hydroxide, and mixtures thereof. The preferred alkaline catalyst is sodium methoxide. The amount of catalyst employed can vary from about 0.01 percent by weight to about 1 percent by weight based on the total weight of the reactants. The amount of alkaline catalyst is not critical. The coupling reaction occurs as the result of an ester interchange. During the reaction, as the temperature is raised from 100° C. up to 200° C., an alcohol is produced which is distilled off thus promoting the ester interchange. The polyoxyalkylene residues are coupled through ester groups to each other and to the residues of the monofunctional alcohol.

The polyoxyalkylene compounds can be prepared by reacting an alkylene oxide with a base compound containing at least one active hydrogen atom as is well known to those skilled in this art. Preferably, the base or initiator compounds have molecular weights of less than 100. The term "active hydrogen atom" is well known to those skilled in the art. It is sufficiently labile to react with ethylene, propylene or butylene oxide and it reacts with methyl magnesium iodide, liberating methane according to the classical Zerewitinoff reaction. The hydrogen atoms are members of a functional group such as a hydroxyl group, a phenol group, a carboxylic acid group, a basic nitrogen group such as an amine group, a hydrazine group, an imine group or an amide group. Hydrogen atoms may be activated by proximity to carbonyl groups such as an acetoacetic ester. Examples of active hydrogen compounds, which may be used as base compounds, include ethylene glycol, diethylene glycol, propylene glycol, dipropylene glycol, butylene glycol, amylene glycol, hexylene glycol, heptylene glycol and octylene glycol.

Using alkylene oxides are ethylene oxide, propylene oxide, butylene oxide and tetrahydrofuran. These can be used either alone or in admixture as is well known to those skilled in the art, to prepare hydrophilic polyoxyalkylenes. The polyoxyalkylene polymers, including copolymers, can have molecular weights of about 104 to about 1000, preferably about 200 to about 1000. The polyoxyalkylene polymers and copolymers employed in this invention are generally prepared by carrying out the condensation reaction of the alkylene oxide with the base compound in the presence of an alkaline catalyst in a manner well known to those skilled in the art. Any of the types of catalysts commonly used for alkylene oxide condensation reactions can be employed. Catalysts which can be employed include sodium hydroxide, potassium hydroxide, sodium methylate, sodium ethylate, potassium acetate, sodium acetate, trimethylamine and triethylamine. After the condensation reaction is completed, the catalyst can be removed from the reaction mixture by any known procedure such as neutralization, filtration or ion exchange. The condensation is preferably carried out at elevated temperatures and pressures. The condensation products are then subjected to the coupling reaction to form the products of the invention.

The monofunctional aliphatic alcohols useful in the invention include the monohydric primary and secondary normal and branched chain aliphatic alcohols preferably having about 6 to about 30 carbon atoms in the alkyl group. Most preferably, about 8 to about 20 carbon atoms are in the alkyl group. Examples of useful monohydric aliphatic alcohols are as follows: n-heptyl alcohol, n-undecyl alcohol, n-dodecyl alcohol, cetyl alcohol, stearyl alcohol, n-nonadecyl alcohol, eicosyl alcohol, ceryl alcohol, palmitoleyl alcohol, 2-methylpentyl alcohol, 3,5-dimethyl-1-hexanol, 4-methyl-2-pentanol, 2,6-dimethyl-4-heptanol, 2,6,8-trimethyl-4-nonanol, n-hexyl alcohol, 2-ethyl-1-butanol, 2-ethyl-1-hexanol, n-octyl alcohol, 2-octyl alcohol, n-nonyl alcohol, n-decyl alcohol, lauryl alcohol, n-tetradecyl alcohol, n-pentadecyl alcohol, octadecyl alcohol, oleyl alcohol, and $C_6$ to $C_{20}$ oxo alcohols.

Useful alkyl monohydric alcohols also include substituted hydrophobic monohydric aliphatic alcohols preferably having a carbon chain of about 6 to about 30 carbon atoms, most preferably about 8 to about 20 carbon atoms. Examples of such substituted monohydric aliphatic alcohols are as follows: the various glycol monoethers such as monoethers of propylene glycol, butylene glycol, polypropylene glycol, polybutylene glycol monoethers, polytrimethtylene glycol and the various glycol mono-formals such as the mixed formals of glycols and $C_6$ to $C_{30}$ alcohols.

Other organic alcohols or derivatives are useful. Examples of these are the hydroxy alkyl ethers of: alkyl-aryl alcohols, i.e., alkyl phenols, and arylalky alcohols. Specific examples are alkoxylated bisphenol A such as the ethoxylated and propoxylated bisphenol A, ethoxylated and propoxylated alkyl phenol, i.e., alkoxylated nonyl phenol.

Any of the monofunctional alcohols set forth above can have substituents which do not contain active hydrogen such as halogen, for example, chlorine, bromine, and iodine, nitrate groups or alkoxy radicals.

The dialkyl esters utilized as coupling agents in the process of the invention are dialkyl carbonates and dialkyl esters of $C_2$ to $C_6$ dicarboxylic acids having 1 to about 7 carbon atoms in each alkyl group. Examples of useful dialkyl ester coupling agents are dimethyl carbonate, diethyl carbonate, diethyl succinate, diethyl oxylate, diethyl maleate, diethyl glutarate, and diethyl adipate. Preferred coupling agents are diethyl carbonate and diethyl succinate. It is noted that during the coupling reaction, the alkyl groups of the dialkyl ester react with water present to form an alkanol which is removed from the reaction medium by distillation, thus promoting the ester interchange reaction resulting in coupling of the reactants through a carbonate or carboxylic acid ester linkage.

The following examples will further illustrate the method of preparation of the ester coupled non-ionic surface-active agents of the invention and their use as surface-active agents. These examples are not to be considered as limiting the scope of the invention. In the specification, claims and examples which follow, all parts, percentages, and proportions are by weight and all temperatures are in degrees centigrade unless otherwise noted.

EXAMPLE 1

This example illustrates the preparation of a carbonate coupled non-ionic surfactant having two units derived from a polyoxyethylene glycol having a molecular weight of 300 and one unit derived from mixed alkyl alcohols having 12 to 15 carbon atoms in the alkyl chain. A one-liter distilling flask equipped with a fractionating column and distillation head was charged with 300 grams of polyethylene glycol having a molecular weight of 300, 101 grams of a mixture of aliphatic monofunctional alcohols having carbon chain lengths in the range of 12 to 15 carbons, sold under the trademark "NEODOL 25", 130 grams of diethyl carbonate, and 1.5 grams of sodium methoxide. The mixture was heated to a temperature of 134° C. at which time ethanol began to distill off. An ethanol distillate was collected in the amount of 68.6 grams over a period of 80 minutes during which the flask temperature rose to 190° C. The crude reaction product was vacuum stripped at a temperature of 120° C. for 25 minutes. An additional 28.2 grams of volatiles were collected during the stripping process. To the stirred product, there was added 10 grams of magnesium silicate and the mixture was stirred at 90° to 100° C. for 30 minutes. One gram of filter aid was then added and the product was filtered to yield 378 grams of a clear, light-brown liquid. The product dissolved in water to give a clear solution. A one percent solution in water was found to have a pH of 8.5. The cloud point, as measured in a one weight percent aqueous solution, was 58° C. The surface tension of a 0.1 weight percent aqueous solution was 32.3 dynes per centimeter, the Draves sink time utilizing a 0.1 weight percent aqueous solution was 82 seconds.

EXAMPLE 2

This example illustrates the preparation of a succinate coupled non-ionic surfactant having three units derived from a polyoxyethylene glycol having a molecular weight of 300 and one unit derived from mixed alkyl alcohols having 12 to 15 carbon atoms in the alkyl chain. A one-liter distilling flask equipped with a fractionating column and distillation head was charged with 338 grams of polyethylene glycol having a molecular weight of 300, 76 grams of a mixture of aliphatic monofunctional alcohols having carbon chain lengths in the range of 12 to 15 carbon atoms, sold under the trademark "NEODOL 25", 196 grams of diethyl succinate, and 3 grams of sodium methoxide. The mixture was heated to a temperature of 117°0 C. at which time ethanol began to distill off. An ethanol distillate was collected in the amount of 89.2 grams over a period of 80 minutes during which the flask temperature rose to 190° C. The crude reaction product was vacuum stripped to a pressure of less than 5 torr. To the stirred product, there was added 10 grams of magnesium silicate and the mixture was stirred at 90° to 100° C. for 30 minutes. One gram of filter aid was then added and the product was filtered to yield a clear, light-brown liquid. The product dissolved in water to give a clear solution. A one percent solution in water was found to have a pH of 5.9. The cloud point, as measured in a one percent aqueous solution, was greater than 100° C. The surface tension of a 0.1 percent aqueous solution was 32.8 dynes per centimeter.

EXAMPLES 3 AND 4

Examples 1 and 2 are repeated substituting respectively a hydrophilic heteric and a hydrophilic block polyoxyalkylene glycol for the polyethylene glycol of Examples 1 and 2. Useful non-ionic surfactants are produced. These polyoxyalkylene glycols prepared by reacting a mixture of ethylene oxide and propylene oxide with ethylene glycol as initiator.

While this invention has been described with reference to certain specific embodiments, it will be recognized by those skilled in this art that many variations are possible without departure from the scope and spirit of the invention.

The embodiments of the invention in which an exclusive priviledge or property is claimed are defined as follows:

1. A composition of matter having the formula

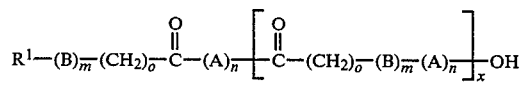

wherein $R^1$ is the residue of at least one hydrophobic $C_{6-30}$ alkanol derived from a compound selected from the group consisting of an alkanol, an aromatic hydrocarbyl alkanol, alkoxylated esters of alkanols, and aromatic hydrocarbyl alkanols an alkoxylated aryl alcohol, and an alkoxylated alkyl aromatic hydrocarbyl alcohol wherein A is the residue of at least one hydrophilic oxyalkylene polymer derived from the same or different alkylene oxides wherein said polymer is selected from the group consisting of heteric, block and homopolymer polyalkylene glycols derived respectively from the reaction of at least 2 alkylene oxides having 2 to 4 carbon atoms or ethylene oxide with an active hydrogen compound having at least two active hydrogen atoms, and wherein B is C=O, m is 0 or 1, x is an integer of 1 to 20, n is individually selected from integers such that the molecular weight is about 104 to about 1000, o is an integer of 0 to 4, and when o is 0, m is 0.

2. A composition of matter having the formula

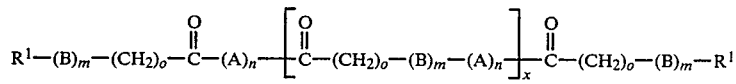

wherein $R^1$ is the residue of at least one hydrophobic $C_{6-30}$ alkanol derived from a compound selected from the group consisting of alkanol an aromatic hydrocarbyl alcohol, alkoxylated esters of alkanols and aromatic hydrocarbyl alkanols, an alkoxylated aryl alcohol, and an alkoxylated alkyl aromatic hydrocarbyl alcohol, wherein A is the residue of at least one hydrophilic oxylkylene polymer derived from the same or different alkylene oxides wherein said polymer is selected from the group consisting of heteric, block, and homopolymer polyalkylene glycols derived respectively from the reaction of at least 2 alkylene oxides having 2 to 4 carbon atoms or ethylene oxide with an active hydrogen compound having at least two active hydrogen atoms, and wherein B is C=O, m is 0 or 1, x is an integer of 1 to 20, n is individually selected from integers such that the molecular weight is about 104 to about 1000, o is an integer of 0 to 4, and when o is 0, m is 0.

3. The composition of claims 1 or 2 wherein A is the residue of an oxyalkylene homopolymer derived from ethylene oxide and $R^1$ is a hydrophobic $C_{8-20}$ alkanol.

4. The composition of claims 1 or 2 wherein A is the residue of an oxyalkylene polymer derived from the reaction of a mixture of ethylene oxide and propylene oxide and $R^1$ is a hydrophobic $C_{8-20}$ alkanol.

5. The composition of claim 4 wherein x is an integer of 1 to 10.

6. The process of forming a nonionic surface-active agent having the formulas of claims 1 or 2 comprising
   (A) mixing reactants (1) a dialkyl ester coupling agent having 1 to 7 carbon atoms in each alkyl group, (2) a hydrophilic polyoxyalkylene glycol having a molecular weight of about 104 to about 1000, and (3) a $C_{6-30}$ alkanol with an alkaline catalyst and a water-immiscible organic reaction solvent;
   (B) reacting at the reflux temperature of the mixture;
   (C) removing the water formed during the reaction azeotropically together with said water-immiscible organic reaction solvent; and
   (D) recovering the desired surface-active agent.

7. The process of claim 6 wherein the amount of akaline catalyst is about 0.01 percent to about 1 percent by weight based upon the total weight of the reactants and wherein said dialkyl ester coupling agent is selected from the group consisting of at least one of a dialkyl carbonate and a dialkyl ester of a $C_2$ to $C_6$ dicarboxylic acid.

8. The process of claim 7 wherein (1) said dialkyl carbonate is diethyl carbonate, (2) said polyoxyalkylene glycol is derived by reacting ethylene oxide with an active hydrogen compound having at least two active hydrogens to prepare a polymer having a molecular weight of about 104 to about 1000, and wherein (3) the third reactant of said mixture is a $C_{6-30}$ alkanol.

9. The process of claim 7 wherein (1) said dialkyl ester is diethyl succinate, (2) said polyoxyalkylene glycol is a heteric or block hydrophilic oxyalklene polymer, and (3) said alcohol is a $C_{8-20}$ alkanol.

* * * * *